US011369714B2

(12) United States Patent
Spragg

(10) Patent No.: US 11,369,714 B2
(45) Date of Patent: Jun. 28, 2022

(54) METHOD FOR PRODUCING COLLAGEN HYDROGELS

(71) Applicant: JELLAGEN PTY LTD, Central Scotland (GB)

(72) Inventor: Andrew Mearns Spragg, Cardiff (GB)

(73) Assignee: JELLAGEN PTY LTD, Stirling (GB)

( * ) Notice: Subject to any disclaimer, the term of this patent is extended or adjusted under 35 U.S.C. 154(b) by 563 days.

(21) Appl. No.: 16/330,862

(22) PCT Filed: Sep. 7, 2017

(86) PCT No.: PCT/GB2017/052607
§ 371 (c)(1),
(2) Date: Mar. 6, 2019

(87) PCT Pub. No.: WO2018/046920
PCT Pub. Date: Mar. 15, 2018

(65) Prior Publication Data
US 2019/0216972 A1    Jul. 18, 2019

(30) Foreign Application Priority Data

Sep. 7, 2016  (GB) .................................... 1615205

(51) Int. Cl.
*A61L 27/24* (2006.01)
*A61L 27/52* (2006.01)
*A61L 27/36* (2006.01)
*A61L 15/32* (2006.01)
*A61L 15/40* (2006.01)
*A61L 15/60* (2006.01)
*A61L 27/38* (2006.01)
*C12N 5/00* (2006.01)

(52) U.S. Cl.
CPC ............. *A61L 15/325* (2013.01); *A61L 15/40* (2013.01); *A61L 15/60* (2013.01); *A61L 27/24* (2013.01); *A61L 27/3604* (2013.01); *A61L 27/3687* (2013.01); *A61L 27/3804* (2013.01); *A61L 27/52* (2013.01); *C12N 5/0068* (2013.01); *A61L 2430/02* (2013.01); *A61L 2430/06* (2013.01); *A61L 2430/16* (2013.01); *A61L 2430/32* (2013.01); *C12N 2513/00* (2013.01); *C12N 2533/54* (2013.01)

(58) Field of Classification Search
None
See application file for complete search history.

(56) References Cited

U.S. PATENT DOCUMENTS 6,660,280 B1    12/2003 Allard et al.
8,105,629 B2     1/2012 Yunoki et al.
2016/0166737 A1*  6/2016 Imhof ................. A61L 27/3604
                                                  424/435

FOREIGN PATENT DOCUMENTS

EP           1723974       11/2006
EP           2181722        5/2010
EP           2644692       10/2013
WO     WO 2005/079879 A1    9/2005
WO     WO 2014/106830       7/2014
WO     WO 2016/166524      10/2016

OTHER PUBLICATIONS

Addad et al., Marine Drugs, 2011, vol. 9, pp. 967-983. (Year: 2011).*
Yunoki et al., Journal of Bioscience and Bioengineering, 2004, vol. 98, No. 1, pp. 40-47. (Year: 2004).*
Office Communication issued in United Kingdom Patent Application No. GB1615205.0, dated Dec. 1, 2016.
PCT International Search Report and Written Opinion issued in International Application No. PCT/GB2017/052607, dated Dec. 6, 2017.
Bosnakovski, Darko, et al. "Isolation and multilineage differentiation of bovine bone marrow mesenchymal stem cells." *Cell and Tissue Research* 319.2 (2005): 243-253.
Drury, Jeanie L., and David J. Mooney, "Hydrogels for tissue engineering: scaffold design variables and applications." *Biomaterials* 24.24 (2003): 4337-4351.
Farndale, R. W., et al. "The role of collagen in thrombosis and hemostasis." *Journal of Thrombosis and Haemostasis* 2.4 (2004): 561-573.
Greenberg, Judith H., et al. "Role of collagen and fibronectin in neural crest cell adhesion and migration," *Developmental Biology* 87.2 (1981): 259-266.
Hennink, Wim E., and Cornelus F. van Nostrum. "Novel crosslinking methods to design hydrogels." *Advanced drug delivery reviews* 64 (2012): 223-236.
Hoffman, Allan S. "Hydrogels for biomedical applications." *Advanced drug delivery reviews* 64 (2012): 18-23.
Hoyer, Birgit, et al. "Jellyfish collagen scaffolds for cartilage tissue engineering." *Acta biomaterialia* 10.2(2014): 883-892.
Leitinger, Birgit, and Erhard Hohenester. "Mammalian collagen receptors." *Matrix Biology* 26.3 (2007): 146-155.
Pozzi, Ambra, et al. "Integrin α1β1 mediates a unique collagen-dependent proliferation pathway in vivo." *The Journal of cell biology* 142.2 (1998): 587-594.
Song, Eun, et al. "Collagen scaffolds derived from a marine source and their biocompatibility." *Biomaterials* 27.15 (2006): 2951-2961.
Willoughby, C. E., M. Batterbury, and S. B. Kaye. "Collagen corneal shields." *Survey of ophthalmology* 47.2 (2002): 174-182.

(Continued)

*Primary Examiner* — Allison M Fox
(74) *Attorney, Agent, or Firm* — ParkerHighlander PLLC

(57) ABSTRACT

The present invention resides in a method for producing jellyfish collagen hydrogels and kits for producing the same. The jellyfish collagen hydrogels can be used in the culture of cells. According to the invention, there is a process for producing jellyfish collagen hydrogels comprising jellyfish collagen fibrils, said process comprising the steps of: mixing a solution of purified jellyfish collagen and an aqueous neutralisation buffer; and incubating the mixture for a sufficient time to enable jellyfish collagen fibrils to form, wherein a cross-linking agent is either added during to mixing step or during or after the incubation of the mixture.

10 Claims, 4 Drawing Sheets

(56) References Cited

OTHER PUBLICATIONS

Koh, Li Buay, et al. "Epoxy cross-linked collagen and collagen-laminin peptide hydrogels as corneal substitutes." *Journal of Functional Biomaterials* 4.3 (2013): 162-177.

Suzuki, K., and K. Morita. "The Effect of Isoionic Point of Gelatin on The Reactivity of Hardener." *Journal-Society of Photographic Science and Technology of Japan* 67.1 (2004): 67-73. English Abstract.

Yunoki, Shunji, Yoshimi Ohyabu, and Hirosuke Hatayama. "Temperature-responsive gelation of type I collagen solutions involving fibril formation and genipin crosslinking as a potential injectable hydrogel." *International Journal of Biomaterials* 2013 (2013).

\* cited by examiner

METHOD FOR PRODUCING COLLAGEN HYDROGELS

This application is a national phase application under 35 U.S.C. § 371 of International Application No. PCT/GB2017/052607, filed Sep. 7, 2017, which claims the benefit of United Kingdom Application No. 1615205.0, filed Sep. 7, 2016, the entirety of each of which is incorporated herein by reference.

FIELD OF INVENTION

The present invention relates to processes for manufacturing collagen assemblies and the products thereof.

BACKGROUND OF THE INVENTION

Collagen is the most ubiquitous protein in the mammalian proteome, comprising up to 30% of all proteins (Leitinger & Hohenester, 2007). It forms a large part of the extracellular matrix and connective tissue, offering strength and flexibility to tissues in the body. Besides its role in mechanical strength, collagen functions as a signalling molecule, regulating cellular migration (Greenberg, et al., 1981), differentiation (Bosnakovski, et al., 2005) and proliferation (Pozzi, et al., 1998), and functions in haemostasis (Farndale, et al., 2004).

The potential of collagen as a biomaterial is made evident by its valuable properties, such as low immunogenicity and cytotoxicity and high tensile strength. To date a plethora of medical uses of collagen have been suggested, developed and applied. Many of these applications make use of collagen when assembled into non-planar substrates or scaffolds. Collagen scaffolds can be used as 3D cell culture matrices (Song, et al., 2006), tissue regeneration scaffolds (Hoyer et al., 2014), corneal shields (Willoughby & Batterbury, 2002), topical wound reparative agents, and vehicles for drug delivery.

One type of collagen scaffold commonly used is the collagen hydrogel. Collagen hydrogels consist of a network of soluble collagen fibres that are prevented from dissociating by polymer entanglement and/or covalent cross-linking. They can also be formed from colloidal suspensions. The physical properties of hydrogels can be tuned depending on the route of manufacture. This topic is covered by several detailed reviews (Drury & Mooney, 2003) (Hennink & van Nostrum, 2012) (Hoffman, 2012).

Collagen hydrogels are rapidly becoming an essential component of modern cell culture techniques. They enable the growth of cells in a 3D lattice more reminiscent of their in vivo environment. The ability to culture cells in vitro in an in vivo environment has obvious benefits for the study of cell biology. 3D hydrogels can also be used as tissue engineering scaffolds, with a particular utility in cartilage repair.

Most commercial sources of collagens are derived from mammalian tissue. Nevertheless it is well known that the use of mammalian collagens in tissue engineering is associated with a considerable risk of virus transmission. Moreover, the purification of collagen from mammalian sources is associated with considerable expense, and contaminant molecules carried over from purification methods impair the reproducibility of mammalian collagen hydrogel formation. This can significantly compromise the reliability of mammalian collagen hydrogels when used in cell culture. Thus, an alternative source of collagen has long been considered desirable.

Collagen extracted from salmon skin has been proposed as an alternative source of collagen for use in manufacturing 3D scaffolds (U.S. Pat. No. 8,105,629). Jellyfish collagen is another potential alternative collagen molecule. Jellyfish collagen has already been successfully employed as a 3D cell culture scaffold in the form of a dehydrated sponge. Jellyfish collagen has been found to be a highly desirable alternative in this endeavour, exhibiting low immunogenicity, low manufacturing costs, and is free from the risk of virus transfer and disease transmission associated with mammalian collagens. Nevertheless, different matrices are beneficial for different clinical and research applications; hence there is still a desire to obtain jellyfish collagen hydrogels. However, the evolutionary constraints imposed upon jellyfish collagen means that the protein has evolved to function optimally at lower temperatures. This lower thermostability has so far precluded the manufacture of jellyfish collagen hydrogels suitable for use at physiological temperatures.

Thus, there is a need for improved methods for manufacturing jellyfish collagen hydrogels suitable for use in cell culture and medical applications.

SUMMARY OF THE INVENTION

This invention is based on the entirely unexpected finding that, despite the vastly different physicochemical properties of jellyfish collagens in comparison with mammalian or fish collagens, jellyfish collagens can be used to form 3D hydrogels stable under physiological conditions.

Accordingly, a first aspect of the invention is process for producing a jellyfish collagen hydrogel comprising jellyfish collagen fibrils, said process comprising: (a) mixing a solution of purified jellyfish collagen and an aqueous neutralisation buffer; and (b) incubating the mixture for a sufficient amount of time to enable collagen fibrils to form, wherein a cross-linking agent is either added during the mixing step (a) or to the collagen fibrils obtained from step (b).

A second aspect of the invention provides a jellyfish collagen hydrogel obtainable from the process defined by the first aspect of the invention. The hydrogel has reversible gelation by being thermally and mechanically responsive.

A third aspect of the invention provides an isolated jellyfish collagen hydrogel, wherein the jellyfish collagen hydrogel is stable at a temperature of from 25° C. to 50° C.

A fourth aspect of the invention utilizes the isolated jellyfish collagen hydrogel of the second or third aspects of the invention in the manufacture of a 3D cell culture scaffold.

A fifth aspect of the invention utilizes the isolated jellyfish collagen hydrogel of the second or third aspects of the invention in the manufacture of a medical device.

A sixth aspect of the invention provides a medical device comprising the jellyfish collagen hydrogel of either the second or third aspect of the invention.

A seventh aspect of the invention provides a 3D cell culture scaffold comprising a jellyfish collagen hydrogel of either of the second or third aspects of the invention.

An eighth aspect of the invention utilizes the 3D cell culture scaffold of the sixth aspect of the invention of culturing cells.

A ninth aspect of the invention provides a kit comprising a solution of purified jellyfish collagen, a neutralisation buffer, and a cross-linking agent.

LIST OF DRAWINGS

Figure 4:
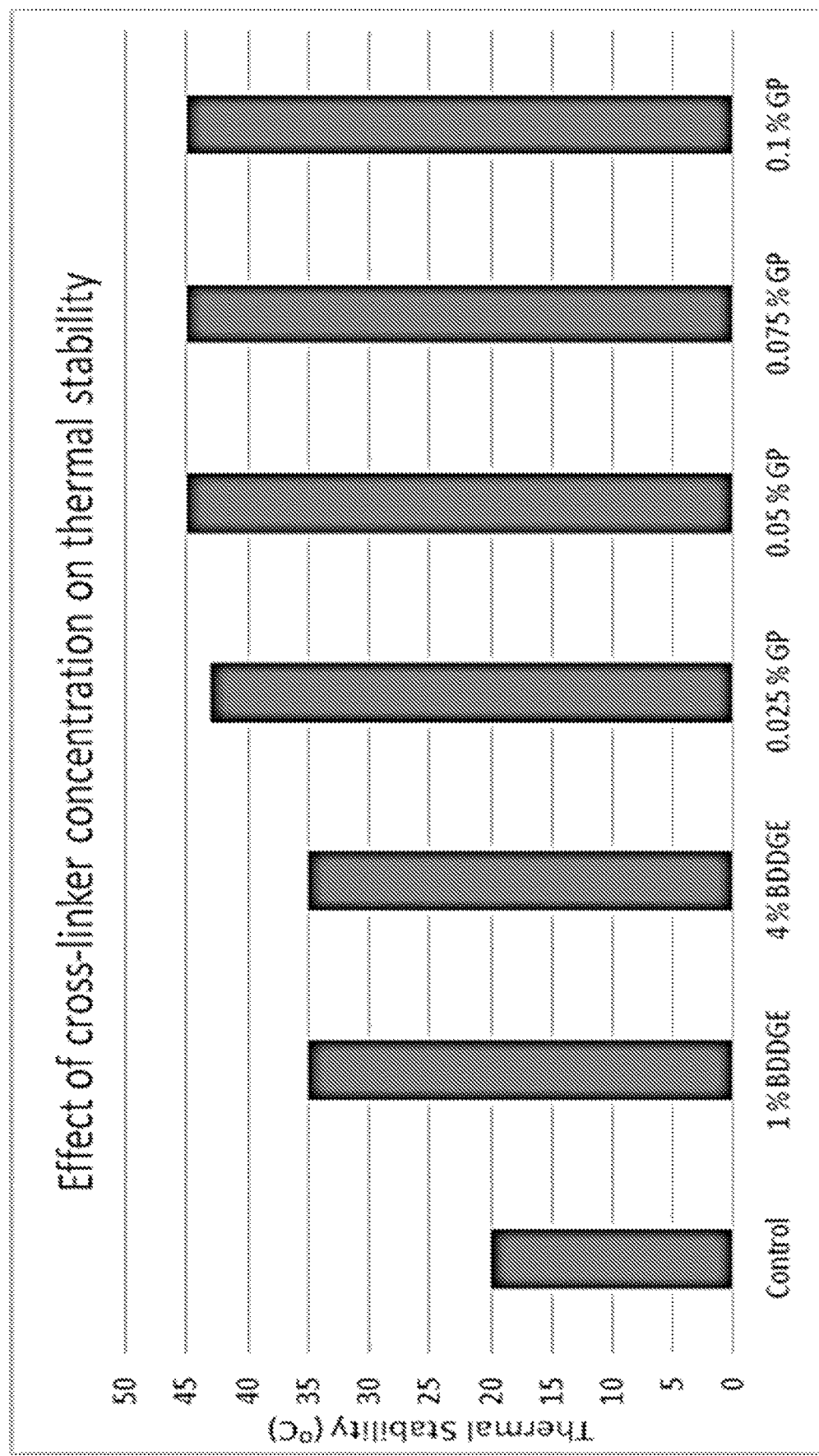

FIG. 4 shows the effect of cross-linker concentration in thermal stability. All gels were formed at pH 7 for 120 h. n=3 for each concentration. Control=JFC hydrogel with no cross-linker, pH 7 after 120 h.

DETAILED DESCRIPTION OF THE INVENTION

The present invention is the realisation of a method that enables the use of jellyfish collagen (JFC) as a viable and practical mammalian collagen-alternative for the construction of hydrogels.

The invention is enabled by the surprising discovery that JFC hydrogels can be formed and made stable at physiological temperatures and pH. Previously, it was not possible to manufacture such hydrogels, due to the low thermostability of JFC. The different environmental conditions and evolutionary distance between mammalian and jellyfish collagens means that JFC has evolved to function optimally at lower temperatures. Moreover, because of the unique physicochemical properties of JFC, the thermodynamic principles that govern the aggregation of JFC are likely to be significantly different compared to those which control the aggregation of mammalian or fish collagens. The robust aggregation of collagen molecules into fibrils is generally required in order to form collagen hydrogels. Thus, in light of the reduced thermostability and the unknown aggregation properties of JFC, it is entirely surprising that JFC can be induced to form collagen hydrogels under conditions similar to those used to form mammalian collagen hydrogels. Furthermore, it is even more surprising, with respect to the reduced thermostability of JFC, that these hydrogels are stable enough under physiological conditions to enable their use as effective substitutes of mammalian and fish collagen hydrogels.

The invention is further described by reference to the following definitions used herein.

A "solution of purified jellyfish collagen" refers to a solution of isolated JFC that is substantially monomeric or, alternatively, substantially free from collagen fibrils. In this context, "substantially free" refers to a solution of collagen with less than 2 wt % of the collagen being composed of fibrils. In order to maintain a collagen solution under these conditions, the isolated collagen can be stored under conditions which disfavour collagen fibril formation. This may mean the collagen is stored under acidic conditions, wherein acidic means any solution with a pH of from pH 1 to pH 6.5, or alternatively under basic conditions, wherein basic means any solution with a pH of from pH 8 to pH 14. By way of non-limiting example, the collagen may be stored in a 0.1 M solution of weak acid. The weak acid may be acetic acid or hydrochloric acid. The concentration of collagen in the collagen solution may be in the range of from 0.1 mg/ml to 30 mg/ml. Preferably, the concentration of the collagen solution is from 1 mg/ml to 10 mg/ml.

There are multiple methods for "isolating", or "purifying", jellyfish collagen from the anatomical milieu. Many of these will be well known and routine to the skilled person. For example, collagen can be purified from jellyfish by acid extraction, whereby different anatomical parts of the jellyfish are bathed in an acidic solution. "Bathing", or "bathed", refers to the process of incubating the jellyfish in the acid solution for a sufficient amount of time in order to liberate the collagen molecule. An alternative method of collagen purification is enzyme extraction, whereby the jellyfish is incubated with at least one proteolytic enzyme for a sufficient amount of time and under conditions that favour the degradation of the anatomical milieu in order to liberate the collagen molecule. The exact temperature, pH and incubation time of the enzyme extraction method will vary depending on the proteolytic enzyme used. The most suitable conditions will be well known to the skilled artisan. By way of non-limiting example, the enzyme pepsin can be incubated with jellyfish under acidic conditions in order to liberate the collagen molecule. It is envisaged that any enzyme can be used in the enzyme extraction method, and the above examples are intended to be in no way limiting.

The collagen can then be further isolated, or purified, from the undesired contaminants of the acid or enzyme extraction method by a number of different means. For example, insoluble contaminants can be removed by centrifugation. If a more pure source of collagen is required, the isolated collagen can be subjected to gel filtration, or an alternative chromatographic method that would enable the purification of the collagen molecule for other soluble contaminants of the extraction process. The exact method of further purification is not particularly limiting. Any method well known and routinely used by a protein biochemist could be adapted for the purpose of obtaining purified, or isolated, jellyfish collagen. This step can also enable the transfer of the jellyfish collagen into the desired storage buffer in order to obtain the desired solution of purified jellyfish collagen. This can be achieved by first equilibrating the chromatographic apparatus with the desired storage buffer before purification. There exist many alternative, well known methods that could be used for this purpose. Preferably, the collagen solution used in the invention is from 70% to 99% pure, wherein pure refers to the % wt in solution attributable to the collagen molecule. More preferably, the collagen solution is at least 95%, 96%, 97%, 98%, or 99% pure.

The term "neutralisation buffer" refers to any buffer within which a solution of purified jellyfish collagen can be diluted in order to increase or decrease the pH to a pH of from pH 4 to pH 9. The composition of the neutralisation buffer is not particularly limiting, only insofar that it must increase or decrease the pH of the solution of purified jellyfish collagen in order that collagen fibril formation can proceed. Furthermore, the buffer must be substantially free from ions, compounds, or molecules which may interfere with any cross-linking process. Thus, a buffer substantially free from unreacted amines is particularly desirable. By way of non-limiting example only, the neutralisation buffer may be of from 1× to 10× phosphate buffered saline (PBS), where 1× or 10× refer to the concentration of PBS. The composition of 1×PBS will be well known to the skilled person. The exact concentration of PBS (i.e. 1× or, e.g. 10×) will depend entirely on the dilution factor required when mixing with the solution of purified jellyfish collagen, in order that the solution of purified jellyfish collagen is substantially neutralised so that collagen fibril formation can proceed. In some embodiments, the neutralisation buffer is sodium hydroxide.

The term "fibril formation", or "fibrillogenesis", refers to the process by which collagen molecules undergo controlled aggregation to form higher order, well-structured macromolecular assemblies. Collagen in vivo is a predominantly extracellular protein whose aggregation into fibrillar structures provides architectural support for surrounding tissues and/or components of the extracellular matrix. The aggregation of collagens, in particular mammalian collagens, is a well-known phenomenon. Different isoforms of mammalian and marine collagens preferentially aggregate into different macromolecular structures. The unique macromolecular structures formed from each collagen isoform is governed by the physicochemical properties of the collagen polypeptide and the conditions under which fibrillogenesis is promoted. Higher-order collagen structures, i.e. collagen fibrils obtained from mammals or fish, have been exploited in vitro in order to generate mammalian and/or fish collagen hydrogels. Thus, in order to form hydrogels from jellyfish collagens, jellyfish collagens are preferred to assemble into higher order structures. Preferably, the higher order structure is a fibril.

The term "cross-linker" or "cross-linking agent" refers to a reactive chemical compound that can, under certain conditions, form covalent linkages between two independent molecules. In the context of the present invention, a cross-linking agent is used to covalently link two independent collagen molecules. Preferably, the collagen molecules to be cross-linked are in the form of collagen fibres. Preferably inter-fibril cross-linking takes place. Cross-linking agents are typically composed of two or more reactive functional groups linked together by a hydrocarbon chain. The two or more functional groups do not necessarily have to be the same. The length of the hydrocarbon chain can also be varied to control the distance between the functional groups. The exact length of the hydrocarbon chain in the context of the present invention is not intended to be limiting. Furthermore, the type of reactive functional group of the cross-linking agent is not particularly limiting. It is envisaged that any cross-linking agent known to cross-link under the conditions within which collagen fibrils are formed would be a suitable cross-linking agent for use in the invention. In certain applications, it may be desirable to use a cross-linking agent that is non-toxic to cells. In certain embodiments, the crosslinking agent may be selected from genipin, 1,4-Butanediol diglycidyl either (1,4-BDDGE), or mucochloric acid. Preferably, the cross-linking agent is either genipin or 1,4-BDDGE. The inclusion of cross-linking agents is particularly advantageous for increasing the thermostability of the hydrogels in order to create a hydrogel stable at a temperature of from 25° C. to 50° C.

Accordingly, a first aspect of the invention provides a process for producing a jellyfish collagen hydrogel comprising jellyfish collagen fibrils, said process comprising: (a) mixing a solution of purified jellyfish collagen and an aqueous neutralisation buffer; and (b) incubating the mixture for a sufficient amount of time to enable collagen fibrils to form, wherein a cross-linking agent is either added during the mixing step (a) or to the collagen fibrils obtained from step (b).

In a preferred embodiment, the mixing step (a) results in a solution of pH from pH 4 to pH 9. Preferably, the mixing step raises the pH to pH 7.4.

In another preferred embodiment, step (b) is performed at a temperature of from 4° C. to 25° C. Although fibrils can be formed outside of this temperature range, this is the optimal temperature range for inducing collagen fibril formation.

In some embodiments, step (b) may be performed for up to 12 hours. In another preferred embodiment, step (b) is performed for from 5 to 60 minutes. The exact time will be dependent upon the temperature employed in step (b), as the temperature will control the kinetics of collagen fibril formation. The skilled person will be able to calculate the optimal time for performing step (b) at different temperatures by following the formation of collagen fibrils over time at different temperatures using spectroscopic techniques. For example, the UV-vis absorption of light of wavelength 313 nm can be measured over time in order to monitor collagen fibril formation. An increase in absorption indicates that fibril formation is proceeding. When the increase plateaus, fibril formation has concluded, thus defining the sufficient amount of time for performing step (b).

In another preferred embodiment, the aqueous neutralisation buffer is phosphate-based.

In another preferred embodiment, the cross-linking agent is selected from genipin, 1,4-BDDGE or mucochloric acid. Preferably, wherein if the cross-linking agent is genipin, it is added at a final concentration of from 0.001% to 5%, preferably at 0.025% (w/v); or if the cross-linking agent is 1,4-BDDGE, it is added at a final concentration of from 0.001% to 5%, preferably at 4% (w/v); or if the cross-linking agent is mucochloric acid, it is added at a final concentration of from 0.001% to 5%, preferably from 0.25% to 4% (w/v). Preferably, the cross-linking agent is genipin or BDDGE.

In another preferred embodiment, the solution of purified jellyfish collagen is purified from a source of collagen by enzyme extraction. The enzyme used in the enzyme extraction method may be selected from pepsin, or a combination thereof. Alternatively, the solution of purified jellyfish collagen is purified from a source of collagen by acid extraction.

In another preferred embodiment, the jellyfish collagen is purified from *Rhizostomas pulmo, Rhopilema esculenturn, Rhopilema nomadica, Stomolophus meleagris, Aurelia* sp., *Nemopilema nomurai*, or combinations thereof. Preferably, the collagen is purified from *Rhizostomas pulmo*.

A second aspect of the invention provides a jellyfish collagen hydrogel obtainable from the process defined by the first aspect of the invention.

A third aspect of the invention provides an isolated jellyfish collagen hydrogel stable at a temperature of from 25° C. to 50° C. Preferably, the hydrogel is stable at up to least 37° C. in cell culture conditions. Cell culture conditions are any conditions under which a mammalian collagen hydrogel could be used as 3D matrix for culturing cells. Stable means that the hydrogel does not substantially denature under the given conditions. Substantial denaturation could, for example, be a loss of >25% of the volume of the hydrogel within 48 h of incubating the hydrogel under the stated conditions.

In a preferred embodiment, the formation of these hydrogels is mechanically reversible, enabling microencapsulation of cells and removal of the hydrogel post-formation of the 3D cell structure. As used herein "mechanically reversible" refers to the mechanical disruption of the hydrogel to form a solution of collagen. This may be advantageous if it is desired to remove the hydrogel at any point, for example, after the construction of a 3D cellular structure has been cultured.

A fourth aspect of the invention utilizes the isolated jellyfish collagen hydrogel of the second or third aspects of the invention in the manufacture of a 3D cell culture scaffold. A cell culture scaffold is a jellyfish collagen hydrogel suitable for culturing cells in vitro in a 3D orientation.

A fifth aspect of the invention utilizes the isolated jellyfish collagen hydrogel of the second or third aspects of the invention in the manufacture of a medical device. Preferably, the medical device is a wound dressing. A wound in the context of the present invention refers to an injury to living tissue caused by a cut, blow, or other impact, that typically results in the skin being cut or broken. A wound dressing is typically designed to cover the wound to provide a sterile environment during healing. A wound dressing may expedite the healing process, for instance when medical agents are applied to the wound dressing on the surface to be contacted to the skin. Collagen is one such reparative agent and acts to attract cells such as fibroblasts and keratinocytes to the wound site in order to enhance tissue repair. The collagen hydrogel can also provide structural support for new tissue growth.

A sixth aspect of the invention provides a medical device comprising the jellyfish collagen hydrogel of either the second or third aspect of the invention. Preferably, the device is a wound healing agent. Alternatively, the medical device may be a corneal shield, cartilage, collection of neurones, or an orthopaedic device.

A seventh aspect of the invention provides a 3D cell culture scaffold comprising a jellyfish collagen hydrogel of either of the second or third aspects of the invention.

An eighth aspect of the invention utilizes the 3D cell culture scaffold of the sixth aspect of the invention of culturing cells. The cell culture scaffold may be used for the culture of primary mammalian cells selected from the list consisting of hepatocytes, myocytes, cardiocytes, keratinocytes, adipocytes, neurons, renal cells, epithelial cells, glial cells, hormone-secreting cells, barrier function cells, extracellular matrix cells, contractile cells, lens cells, stem cells, mesenchymal stem cells, blood-derived stem cells, induced pluripotent stem cells, or a combination thereof. In some embodiments, the cell culture scaffold may be used in the culture of hepatocytes. In some embodiments, the cell culture scaffold may be used in the culture of cardiocytes. In some embodiments, the primary cells are human. The use of the 3D scaffold for culturing cells can enable the growth of 3D cellular structures that may have a variety of research and medical applications. For example, the scaffold could be used to engineer new tissue for surgical transplantation. Such tissues by way of example may be a corneal shield, bone, neurones or cartilage. Other tissues that can be grown using the jellyfish collagen hydrogel as a scaffold will be well known to the skilled artisan.

In another aspect of the invention, there is provided a kit comprising a solution of purified jellyfish collagen, a neutralisation buffer and a cross-linking agent. The kit may comprise any of the embodiments of each of the components as described herein.

The invention is further described with reference to the following non-limiting examples.

EXAMPLES

Example 1: Extraction of Jellyfish Collagen

Extraction of Acid Soluble Collagen from *Rhizostoma pulmo*

Jellyfish (*Rhizostoma pulmo*) material was passed through a 400 μm filter and the retentate was frozen for later use. Frozen tissue was defrosted over 24 hrs with regular stirring. Once fully defrosted, the tissue was brought to pH 13 with 50% NaOH and left for a further 24 h. After 24 h, concentrated acetic acid was added to a concentration of 0.5 M and the pH adjusted to 3.0 with the use of HCl. The tissue was then left for 3-5 days to yield a viscous solution of very low solid content. All steps were carried out at 4° C.

Collagen Purification

The solution was centrifuged for 1 h at 20000 RCF to remove any remaining solid matter. After centrifugation the collagen was precipitated from solution by addition of NaCl to a concentration of 1 M and subsequently centrifuged for a further 20 min to obtain the precipitated collagen. The pellet was then re-suspended in 0.1M acetic acid and the pH adjusted to pH 3 with concentrated HCl. The resulting solution was further centrifuged for a total of 10 h and then diafiltered with 0.1 M acetic acid through a Sartorius Vivaflow 200 system incorporating a 100 kDa membrane filter for 6 diavolumes until a colourless and transparent JFC solution was obtained. Again, all steps were carried out at 4° C.

Example 2: Influence of Solution Conditions on JFC Hydrogel Formation

Fibrillogenesis Assay of JFC—Acid Soluble pH Dependence.

Figure 1:
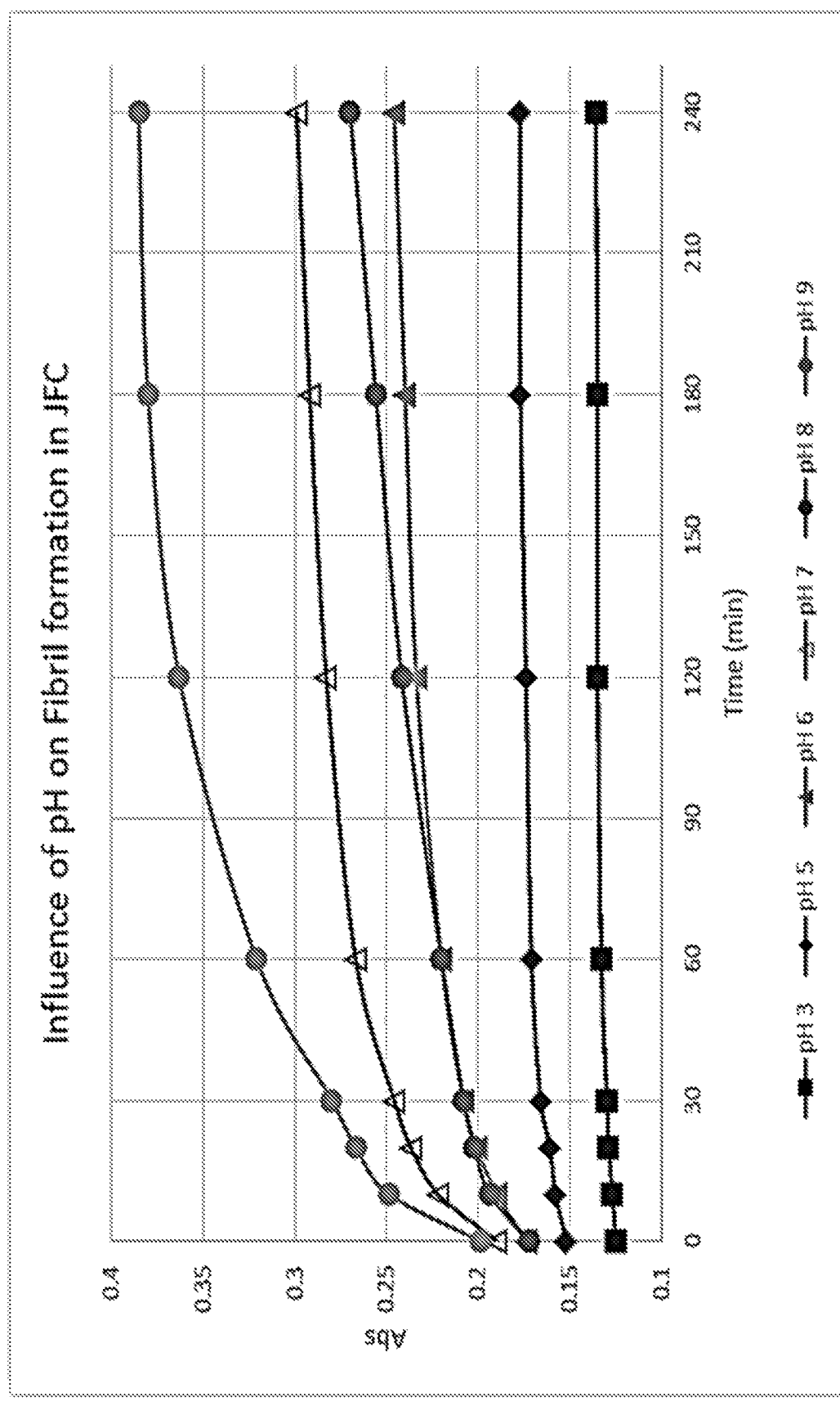
FIG. 1 shows the influence of pH on fibril formation in jellyfish collagen.

Acid soluble JFC was diluted to 3 mg/ml and added to 10× phosphate buffered saline (PBS) to a ratio of 9:1. The pH of the samples was adjusted to pH 3, 5, 6, 7, 8, and 9 using 1 M NaOH (FIG. 1). The samples were then added in triplicate to UV-vis cuvettes and regular absorbance readings were taken at 313 nm until a plateau was reached.

FIG. 1 shows that fibrillogenesis of JFC can occur in solution at a pH of from pH 6 to pH 9.

Fibrillogenesis Assay of JFC—Influence of NaCl Concentration.

Acid soluble JFC was diluted to 3 mg/ml and the pH of the solution adjusted to pH 7.4 using 1 M NaOH. 10×PBS containing 0 M, 0.69 M, 1.38 M and 2.74 M NaCl was then added to a ratio of 9:1 JFC to 10×PBS and the pH adjusted to pH 7.4 again if required. Samples were then added in triplicate to UV-vis cuvettes and regular absorbance readings were taken at 313 nm until a plateau was reached (FIG. 2).

Figure 2:
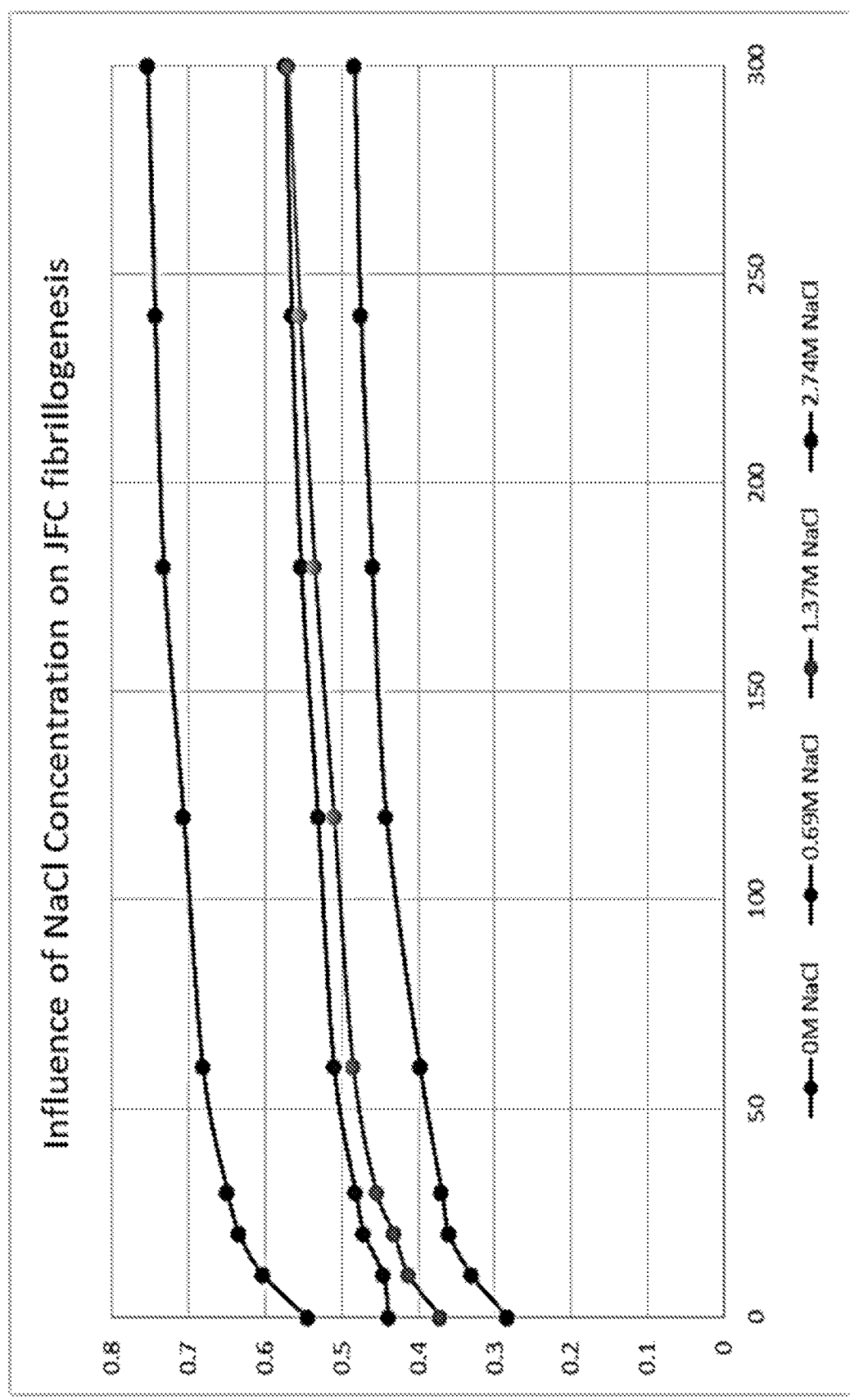
FIG. 2 shows the influence of NaCl concentration on jellyfish collagen (JFC) fibrillogenesis.

FIG. 2 shows that the concentration of NaCl does not significantly impact upon JFC fibrillogenesis.

Formation of Jellyfish Collagen Hydrogels—Influence of pH and Temperature.

JFC was gelled by adding 10×PBS to a 3 mg/ml sample of acid soluble JFC to a ratio of 9:1 JFC to PBS. NaOH was added to adjust the solution to pH 3, 5, 6, 7, 8 and 9. Samples from each pH were then left at either 4° C. or 19° C. for 8 h to allow the gel to develop.

Under the conditions employed, JFC fibril formation and gelation takes place best at 4° C.

Determination of Thermostability

The thermostability of hydrogels was studied using hydrogels formed in PBS at pH 9 and at 4° C. The JFC solution was supplemented with 2.74 M NaCl. The resulting JFC hydrogels were immersed in a water bath for 5 min at either 18° C., 20° C., 22° C., 24° C. and 26° C. The denaturation temperature was determined as the point at which half the gel collapsed.

FIG. 4 shows that in the absence of a cross-linker the hydrogel has a thermostability of around 20° C.

Example 3: Increasing the Thermostability of Hydrogels

The ability of the cross-linkers genipin, BDDGE, and muchochloric acid to increase the thermal stability of jellyfish collagen (JFC) hydrogels were evaluated with the aim of creating a JFC hydrogel that is stable for long periods of time at >37° C.

Preparation of Jellyfish Collagen (JFC) Gels.

Multiple aliquots of 3.5 mg/ml of acid solubilized JFC were diluted with 10× phosphate buffered saline (PBS) ar a ratio of 9:1 (JFC: 10×PBS). Each solution was then pH-adjusted to between pH 3 and pH 9 by adding concentrated NaOH. The cross-linking agents 1,4-BDDGE, genipin or mucochloric acid, were then added to a final concentration of from 1% to 4%, or from 0.025% to 5%, or from 0.1% to 5%, respectively. The solutions were then stirred to allow diffusion of the cross-linker, and incubated at from 4° C. to 25° C. for from 0.5 h to 24 h to allow fibrillogenesis and gelation to complete.

Determination of Thermal Stability

Figure 3:
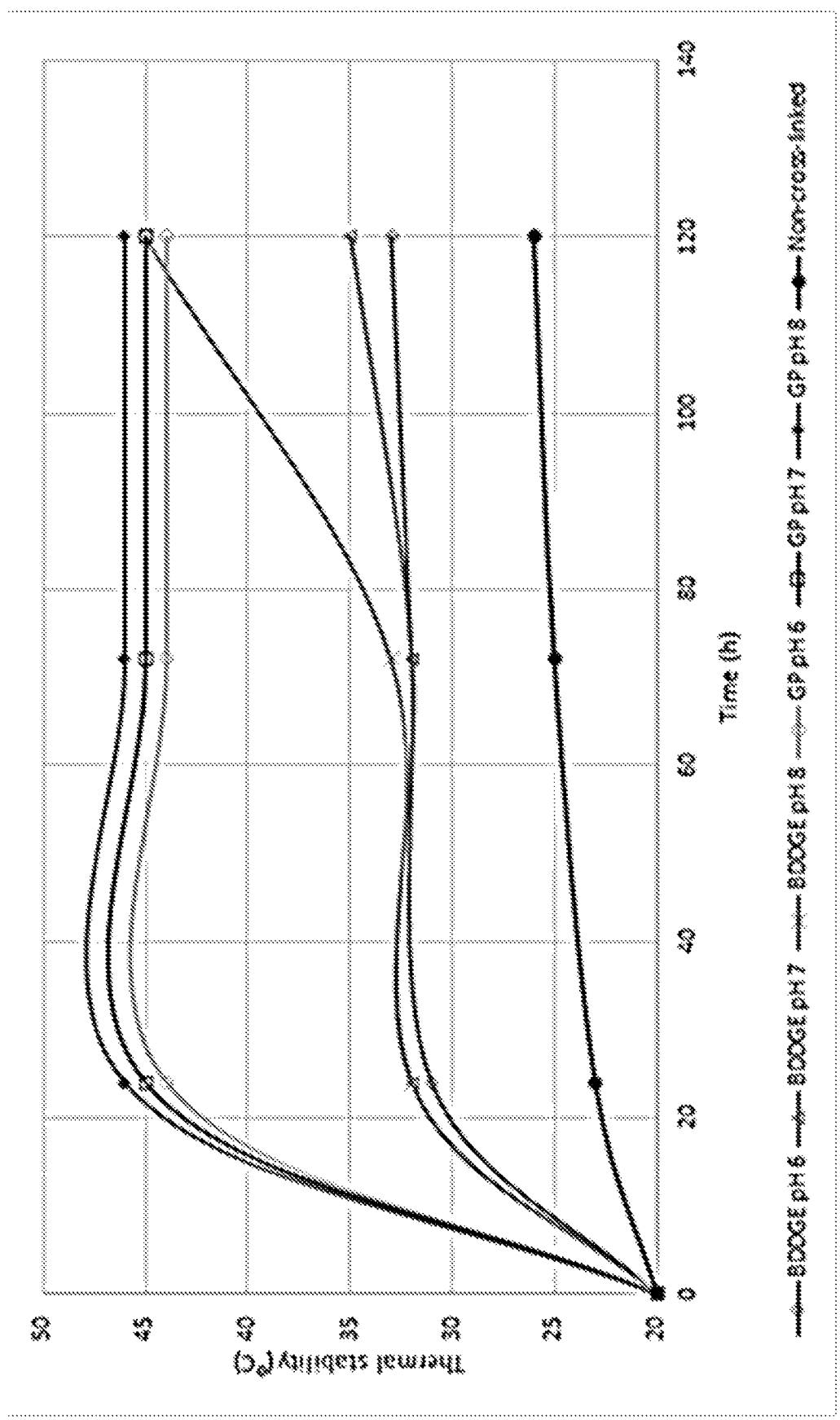
FIG. 3 shows the effect of time and pH on the thermostability of BDDGE or genipin (GP) cross-linked collagen fibril hydrogels.

In order to determine thermostability the cross-linked gels were placed in an incubator at 20° C. The temperature was increased by 1° C. every hour and the thermostability was recorded (FIG. 3). The thermostability was defined as the temperature at which the gels first began to shrink and/or melt and shall be here on in referred to as $T_m$.

The evolution of the thermostability of hydrogels cross-linked with either 1% BDDGE or 0.1% genipin hydrogels over time was investigated in a range of pH solutions (FIG. 3). This was performed in order to determine whether time or pH have an effect on hydrogel thermostability. FIG. 3 shows that, irrespective of pH, BDDGE-cross-linked hydrogels experience an increase in thermostability of approximately of 13° C. during the initial 24 h. The thermostability then plateaus, until 72 h, at which point a steady increase in the thermostability of the hydrogel is observed at pH 8 (after 120 h, thermostability of 45° C.).

By contrast, JFC hydrogels cross-linked with genipin did not show a time-dependent or pH-dependent increase in thermostability after 24 h. The thermostability of genipin-cross-linked hydrogels increases to approximately 45° C. after 24 h irrespective of the pH (FIG. 3).

Thus, genipin-cross-linked hydrogels have a greater thermostability than hydrogels cross-linked with BDDGE, except for BDDGE-cross-linked hydrogels when incubated at pH 8 for 120 h.

Thermal Stability of Hydrogels, Cross-Linked at Different Concentrations of BDDGE and GP Two concentrations of both genipin and BDDGE were used in order to determine the lowest possible concentrations of each cross-linker that would allow the formation of a hydrogel stable at 37° C. Cross-linked hydrogels were formed with 1% and 4% BDDGE (v/v) and 0.025%, 0.05%, 0.075% and 0.1% genipin at pH 7 for 120 h and the effects on $T_m$ are shown in (FIG. 4). As can be seen, the 1% BDDGE hydrogel had exactly the same $T_m$ as the 4% BDDGE hydrogel. Both concentrations resulted in an increase in $T_m$ of 15° C., from 20° C. in the uncross-linked hydrogel, to 35° C. in both the 1% and 4% cross-linked hydrogels. Neither concentration produced a hydrogel stable at 37° C., as they were not incubated at pH 8.0. All of the genipin concentrations produced hydrogels thermostable at 37° C. with the lowest $T_m$ being 43° C. in the 0.025% genipin-cross-linked hydrogel (FIG. 4). This is 23° C. higher than the non-cross-linked control. The three higher concentrations of 0.05%, 0.075% and 0.1% GP all had a $T_m$ of 45° C.

Thus, cross-linking hydrogels with any of the above concentrations of genipin produces hydrogels with a $T_m$ in excess of 37° C. (FIG. 4).

The invention claimed is:

1. A process for producing a jellyfish collagen hydrogel comprising jellyfish collagen fibrils, said process comprising:
    (a) mixing:
        (i) a solution of purified jellyfish collagen; and
        (ii) an aqueous neutralisation buffer; and
    (b) incubating the mixture for a sufficient amount of time to enable collagen fibrils to form,
    wherein a cross-linking agent is either added during the mixing step (a) or to the collagen fibrils obtained from step (b).

2. The process of claim 1, wherein the mixing step (a) results in a solution having a pH of from pH 4 to pH 9.

3. The process according to claim 1, wherein step (b) is performed at a temperature of from 4° C. to 25° C.

4. The process according to claim 1, wherein the sufficient amount of time is for up to 12 hours.

5. The process according to claim 1, wherein the aqueous neutralisation buffer is phosphate-based.

6. The process according to claim 1, wherein the cross-linking agent is selected from genipin, 1,4-Butanediol diglycidyl either (1,4-BDDGE), or mucochloric acid.

7. The process according to claim 1, wherein the solution of purified jellyfish collagen has been purified from a source of collagen by enzyme extraction.

8. The process according to claim 1, wherein the solution of purified jellyfish collagen has been purified from a source of collagen by acid extraction.

9. The process according to claim 1, wherein the solution of purified jellyfish collagen has been purified from *Rhizostomas pulmo*, *Rhopilema esculentum*, *Rhopilema nomadica*, *Stomolophus meleagris*, *Aurelia* sp., *Nemopilema nomurai*, or combinations thereof.

10. The process according to claim 1, wherein the sufficient amount of time is from 5 to 60 minutes.

* * * * *